(12) United States Patent
Gallou et al.

(10) Patent No.: US 9,604,914 B2
(45) Date of Patent: Mar. 28, 2017

(54) PROCESS FOR PREPARING N-(4-CYCLOHEXYL-3-TRIFLUOROMETHYL-BENZYLOXY)-ACETIMIDIC ACID ETHYL ESTER

(71) Applicant: NOVARTIS AG, Basel (CH)

(72) Inventors: Fabrice Gallou, Basel (CH); Joerg Matthias Sedelmeier, Basel (CH); Caspar Vogel, Basel (CH)

(73) Assignee: NOVARTIS AG, Basel (CH)

(*) Notice: Subject to any disclaimer, the term of this patent is extended or adjusted under 35 U.S.C. 154(b) by 0 days.

(21) Appl. No.: 14/376,143

(22) PCT Filed: Feb. 1, 2013

(86) PCT No.: PCT/EP2013/052106
§ 371 (c)(1),
(2) Date: Aug. 1, 2014

(87) PCT Pub. No.: WO2013/113915
PCT Pub. Date: Aug. 8, 2013

(65) Prior Publication Data
US 2015/0018577 A1 Jan. 15, 2015

Related U.S. Application Data

(60) Provisional application No. 61/594,591, filed on Feb. 3, 2012.

(51) Int. Cl.
| | | |
|---|---|---|
| C07C 249/12 | (2006.01) | |
| C07D 205/04 | (2006.01) | |
| C07C 47/55 | (2006.01) | |
| C07C 22/08 | (2006.01) | |
| C07C 17/12 | (2006.01) | |
| C07C 17/14 | (2006.01) | |
| C07C 17/26 | (2006.01) | |
| C07C 17/35 | (2006.01) | |
| C07C 17/354 | (2006.01) | |
| C07C 25/18 | (2006.01) | |
| C07C 259/04 | (2006.01) | |
| C07C 33/50 | (2006.01) | |
| C07C 49/82 | (2006.01) | |
| C07C 17/04 | (2006.01) | |
| C07C 29/14 | (2006.01) | |
| C07C 29/147 | (2006.01) | |
| C07C 29/44 | (2006.01) | |
| C07C 45/27 | (2006.01) | |

(Continued)

(52) U.S. Cl.
CPC ............ *C07C 249/12* (2013.01); *C07C 17/04* (2013.01); *C07C 17/12* (2013.01); *C07C 17/14* (2013.01); *C07C 17/26* (2013.01); *C07C 17/35* (2013.01); *C07C 17/354* (2013.01); *C07C 22/08* (2013.01); *C07C 25/18* (2013.01); *C07C 29/14* (2013.01); *C07C 29/147* (2013.01); *C07C 29/44* (2013.01); *C07C 33/50* (2013.01); *C07C 45/27* (2013.01); *C07C 47/55* (2013.01); *C07C 49/82* (2013.01); *C07C 51/15* (2013.01); *C07C 251/52* (2013.01); *C07C 259/04* (2013.01); *C07D 205/04* (2013.01); *C07C 2101/14* (2013.01); *C07C 2101/16* (2013.01)

(58) Field of Classification Search
None
See application file for complete search history.

(56) References Cited

U.S. PATENT DOCUMENTS

| | | | |
|---|---|---|---|
| 3,452,079 A | 6/1969 | Shen et al. | |
| 4,404,384 A * | 9/1983 | Gebert | C07C 255/00 540/609 |

(Continued)

FOREIGN PATENT DOCUMENTS

| | | |
|---|---|---|
| GB | 1153206 A | 5/1969 |
| JP | 2009-114141 A | 5/2009 |

(Continued)

OTHER PUBLICATIONS

Khomutov et al. Hydroxylamine Derivatives: Synthesis of Some O-Substituted Hydroxylamines, 1967, 1743-1745.*

(Continued)

*Primary Examiner* — Clinton Brooks
(74) *Attorney, Agent, or Firm* — James Lynch

(57) ABSTRACT

This invention relates to novel processes for synthesizing N-(4-cyclohexyl-3-trifluoromethyl-benzyloxy)-acetimidic acid ethyl ester and to the compound of formula I below and other intermediates that are used in such processes.

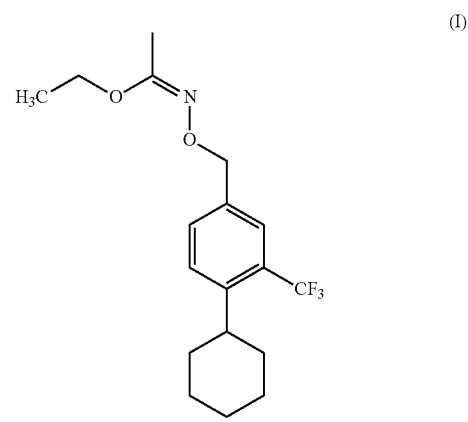

(I)

14 Claims, No Drawings

(51) Int. Cl.
*C07C 51/15* (2006.01)
*C07C 251/52* (2006.01)

(56) References Cited

U.S. PATENT DOCUMENTS

| | | | |
|---|---|---|---|
| 6,596,877 B2 * | 7/2003 | Shieh | C07C 41/16 548/343.5 |
| 2007/0203100 A1 | 8/2007 | Pan et al. | |
| 2009/0036423 A1 * | 2/2009 | Pan | C07C 251/48 514/210.17 |
| 2009/0324581 A1 * | 12/2009 | Machinaga | A61K 31/404 424/130.1 |
| 2010/0113528 A1 | 5/2010 | Ahmed et al. | |

FOREIGN PATENT DOCUMENTS

| | | |
|---|---|---|
| WO | 2004103306 A2 | 12/2004 |
| WO | 2005/082089 A2 | 9/2005 |
| WO | 2005082841 A1 | 9/2005 |
| WO | 2008074820 A1 | 6/2008 |

OTHER PUBLICATIONS

Johnson J E et al: "Synthesis and Configurations of 0-Substituted Hydroximoyl Chlorides. Stereochemistry and Mechanism of Alkoxide Ion Substitution at the Carbon-Nitrogen Double Bond", Journal of Organic Chemistry, ACS, US, vol. 50, No. 7, 1985, pp. 993-997.

* cited by examiner

PROCESS FOR PREPARING N-(4-CYCLOHEXYL-3-TRIFLUOROMETHYL-BENZYLOXY)-ACETIMIDIC ACID ETHYL ESTER

This invention relates to novel processes for synthesizing N-(4-cyclohexyl-3-trifluoromethyl-benzyloxy)-acetimidic acid ethyl ester and to intermediates that are used in such processes.

BACKGROUND OF THE INVENTION

The compound N-(4-cyclohexyl-3-trifluoromethyl-benzyloxy)-acetimidic acid ethyl ester is an intermediate in the synthesis of the pharmaceutically active compound 1-{4-[1-(4-cyclohexyl-3-trifluoromethyl-benzyloxyimino)-ethyl-benxyl}-azetidine-3-carboxylic acid ("Compound A"). Compound A is a sphingosine-1-phosphate ("S1P") modulator that is useful for the treatment of immunological disorders, e.g., multiple sclerosis. Compound A, methods of synthesizing Compound A and methods of treating various disorders using Compound A are referred to in U.S. Pat. No. 7,939,519, which issued on May 10, 2011. This patent is incorporated herein by reference in its entirety.

SUMMARY OF THE INVENTION

This invention relates to the compound having the formula

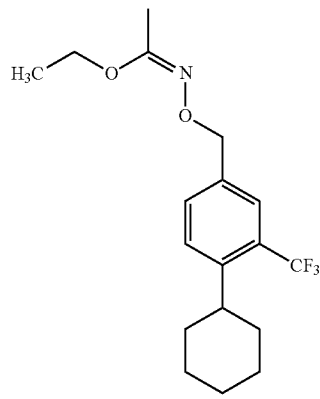

(I)

and the chemical name N-(4-Cyclohexyl-3-trifluoromethyl-benzyloxy)-acetimidic acid ethyl ester. This compound is an intermediate in the synthesis of Compound A.

This invention also relates to the compound having the formula

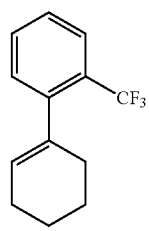

(IV)

This compound is useful as an intermediate in the syntheses of both the compound of formula I and Compound A.

This invention also relates to compounds of the formula

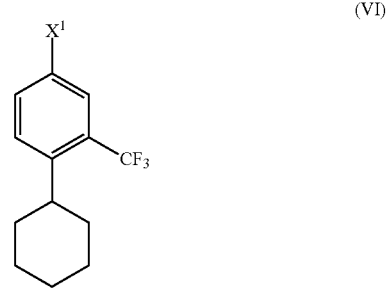

(VI)

wherein $X^1$ is bromo, chloro, iodo or fluoro, preferably bromo. These compounds are useful as intermediates in the syntheses of both Compound A and the compound of formula I.

This invention also relates to the compound of formula

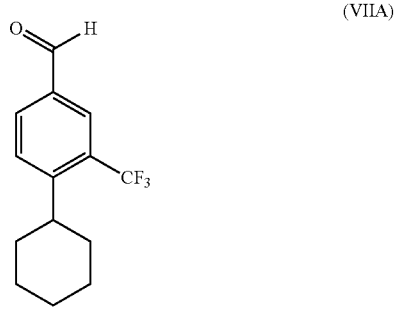 [SMILES: O=Cc1ccc(C2CCCCC2)c(C(F)(F)F)c1]

(VIIA)

This compound is useful as an intermediate in the syntheses of both Compound A and the compound of formula I.

This invention also relates to the compound of formula

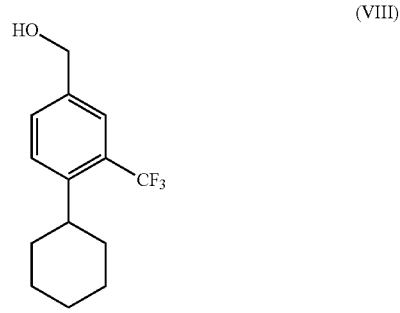

(VIII)

This compound is useful as an intermediate in the syntheses of both the compound of formula I and Compound A.

This invention also relates to the compound of formula

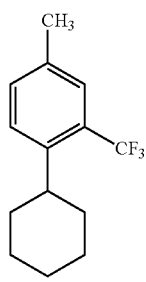
(XIII)

This compound is useful as an intermediate in the syntheses of both Compound A and the compound of formula I.

This invention also relates to the compound of formula

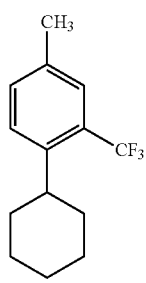
(XIV)

This compound is useful as an intermediate in the syntheses of both Compound A and the compound of formula I.

This invention also relates to the compound of formula

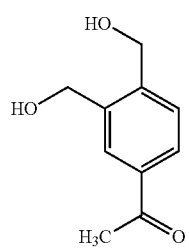
(XXI)

This compound is useful as an intermediate in the synthesis of Compound A from the compound of formula I.

This invention also relates to a process for preparing the compound of formula I, as described above, comprising reacting a compound having the formula

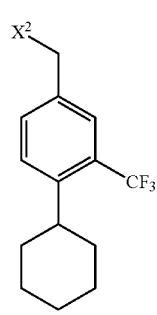
(IX)

wherein $X^2$ is bromo, chloro, iodo, mesylate, tosylate, brosylate, triflate or another suitable leaving group, preferably bromo, with the compound of formula

(X)

wherein Et is ethyl, in the presence of: (i) a strong base, preferably sodium hydride or potassium t-butoxide or, alternatively, a weaker base such as potassium carbonate or sodium carbonate; and (ii) a catalytic amount of 4-dimethylamino pyridine.

This invention also relates to the above method for preparing the compound of formula I from a compound of the formula IX, wherein the starting material of formula IX is prepared by a process comprising:

(a) reacting a compound of the formula

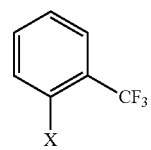
(II)

wherein X is bromo or iodo, preferably bromo, with an appropriate Grignard reagent (preferably, when X is bromo, i-propylmagnesiumchloride lithium chloride complex) and cyclohexanone to form the compound of formula

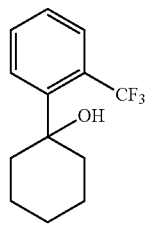
(III)

(b) reacting the compound of formula III with a strong acid, preferably sulfuric acid, to form the compound of formula

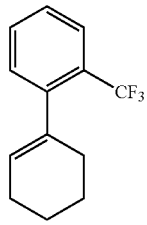
(IV)

(c) subjecting the compound of formula IV to catalytic hydrogenation to form the compound of formula

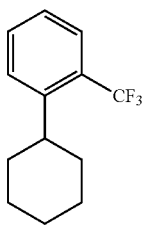

(d) converting the compound of formula V into a compound of the formula (VI)

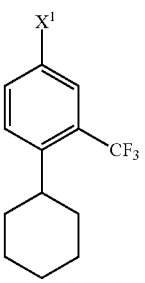

wherein $X^1$ is bromo, chloro, iodo or fluoro, preferably bromo, by reacting the compound of formula V with 1,3-dibromyl-5,5-diethylhydantoin when $X^1$ is bromo, or with the appropriate analogous compound when $X^1$ is chloro, fluoro or iodo, in the presence of an acid, preferably trifluoroacetic acid or a mixture of sulfuric acid and trifluoroacetic acid;

(e) reacting the compound of formula VI with an appropriate Grignard reagent, preferably a butyl lithium butylmagnesium chloride complex, and carbon dioxide to form the compound of formula (VII)

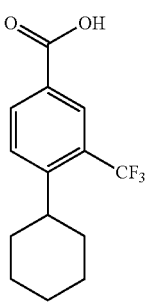

(f) reducing the compound of formula VII, preferably using lithium aluminum hydride, to form the compound of formula (VIII)

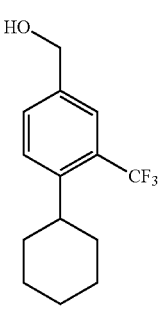

and (g) subjecting the compound of formula VIII to a reaction that replaces the hydroxy group of formula VIII a leaving group, preferably by: (i) reacting the compound of formula VIII with the appropriate compound of the formula $HX^2$, wherein $X^2$ is defined as it is for formula IX above, to form a compound of the formula IX wherein $X^2$ is chloro, bromo or iodo; or (ii) reacting the compound of formula VIII with the mesyl chloride, trifluoromesyl chloride or tosyl chloride to form a compound of the formula IX wherein $X^2$ is mesylate, triflate or tosylate.

This invention also relates to the above method for preparing a compound of the formula I from a compound of the formula IX, as described above, wherein the starting material of formula IX is prepared by a process comprising:

(a) reacting a compound of the formula (XI)

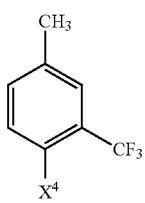

wherein $X^4$ is bromo, chloro or iodo, with the compound of formula (XII)

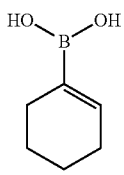

in the presence of a palladium catalyst, preferably palladium acetate, a phosphine, preferably triphenylphosphine, and a base, preferably, sodium methylate, to form the compound of formula (XIII)

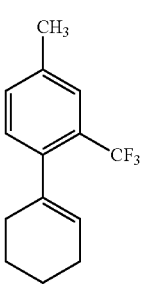

(b) subjecting the compound of formula XIII to catalytic hydrogenation to form the compound of formula (XIV)

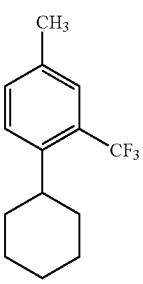

(c) subjecting the compound of formula XIV to radical bromination, preferably via reaction with N-bromosuccinimide, or radical chlorination, preferably via reaction with N-chlorosuccinimide, to yield a compound of the formula IX wherein $X^2$ is bromo or chloro, respectively.

This invention also relates to a process for preparing the compound of formula I, as described above, from a compound of formula IX, wherein the starting material of formula IX is prepared by a process comprising:

(a) reducing a compound of the formula

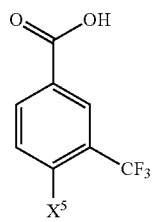
(XV)

wherein $X^5$ is chloro, bromo or iodo, to form the corresponding compound of formula

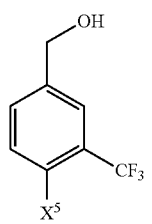
(XVI)

wherein $X^5$ is chloro, bromo or iodo;

(b) reacting the resulting compound of formula XVI with the compound of formula

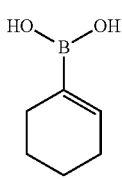
(XII)

in the presence of a palladium catalyst and a base, preferably in the presence of bistriphenylphosphinepalladiumdichloride and either potassium carbonate or sodium methylate, to form the compound of formula

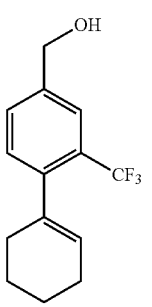
(XVII)

(c) subjecting the compound of formula XVII to catalytic hydrogenation to form the compound of formula

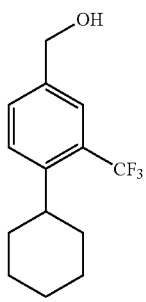
(VIII)

and (d) subjecting the compound of formula XVIII to a reaction that replaces the hydroxy group of formula VIII with a leaving group, preferably by: (i) when $X^2$ in formula IX is chloro, fluoro or iodo, reacting the compound of formula VIII with the appropriate compound of the formula $HX^2$, wherein $X^2$ is defined as it is for formula IX; or (ii) when $X^2$ in formula IX is mesylate, triflate or tosylate, reacting the compound of formula VIII with mesyl chloride, trifluoromesyl chloride or tosyl chloride, respectively.

This invention also relates to the process for forming the compound of formula I from a compound of the formula IX, as described above, wherein the starting material of formula IX is prepared by a process comprising:

(a) reacting a compound of the formula

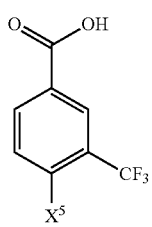
(XV)

wherein $X^5$ is chloro, bromo or iodo, with the compound of formula

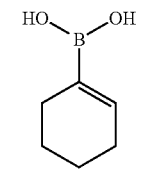
(XII)

in the presence of a palladium catalyst and a base, preferably in the presence of bistriphenylphosphinepalladiumdichloride and either potassium carbonate or sodium methylate, to form the compound of formula (XIX)

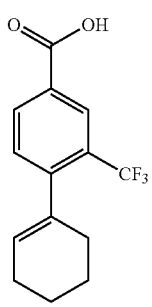

(b) subjecting the compound of formula XIX to catalytic hydrogenation to form the compound of formula (VII)

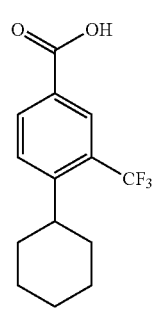

(c) reducing the compound of formula VII, preferably using lithium aluminum hydride, to form the compound of formula (VIII)

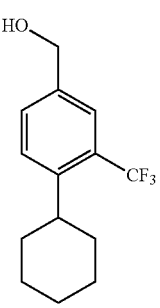

and (d) subjecting the compound of formula VIII to a reaction that replaces the hydroxy group of formula VIII a leaving group, preferably by: (i) when $X^2$ in formula IX is chloro, bromo or iodo, reacting the compound of formula VIII with the appropriate compound of the formula $HX^2$, wherein $X^2$ is defined as it is for formula IX; or (ii) when $X^2$ in formula IX is mesylate, triflate or tosylate or brosylate, reacting the compound of formula VIII with mesyl chloride, trifluoromesyl chloride, tosyl chloride or brosyl chloride, respectively.

DETAILED DESCRIPTION OF THE INVENTION

In the discussion and reaction schemes that follow, X, $X^1$, $X^2$, $X^3$, $X^4$ and $X^5$ are defined as they are defined above.

The compounds and processes of this invention are depicted below in reaction Schemes I-V.

SCHEME I

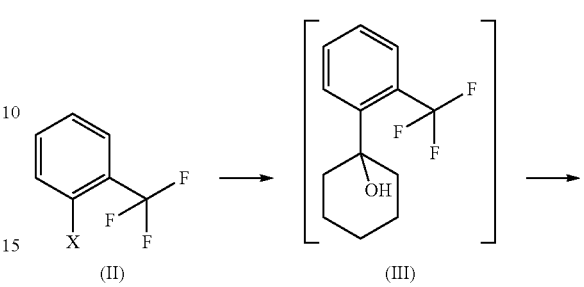

(II)     (III)

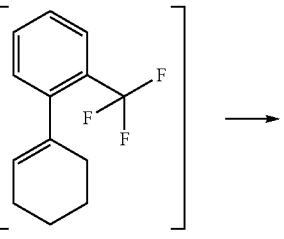

(IV)

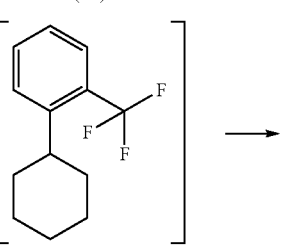

(V)

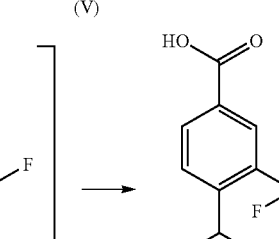

(VI)     (VII)

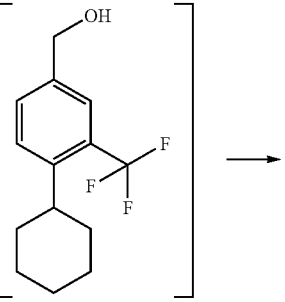

(VIII)

SCHEME III
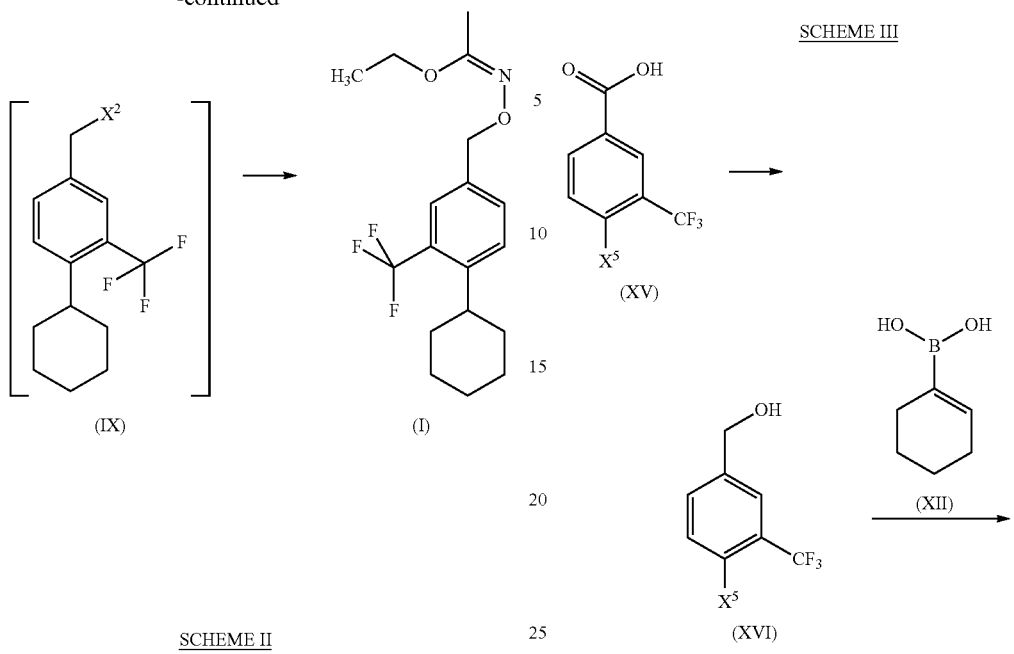
SCHEME II
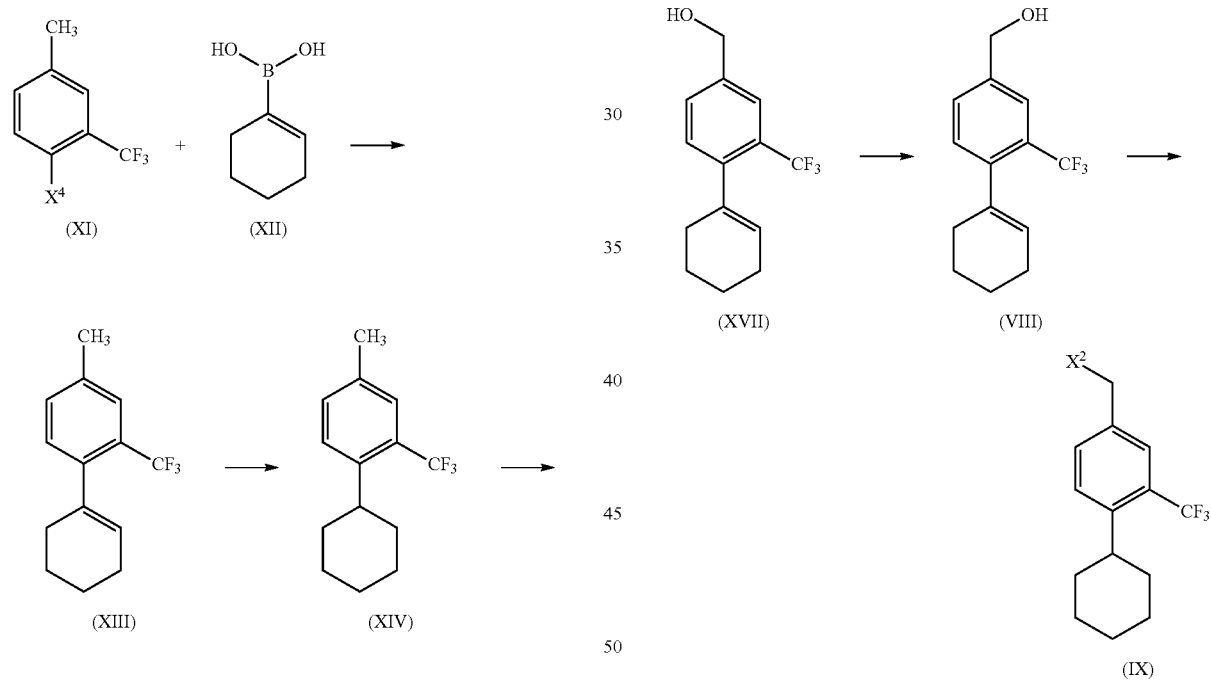
SCHEME IV
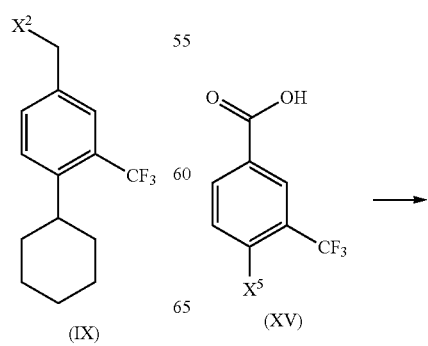

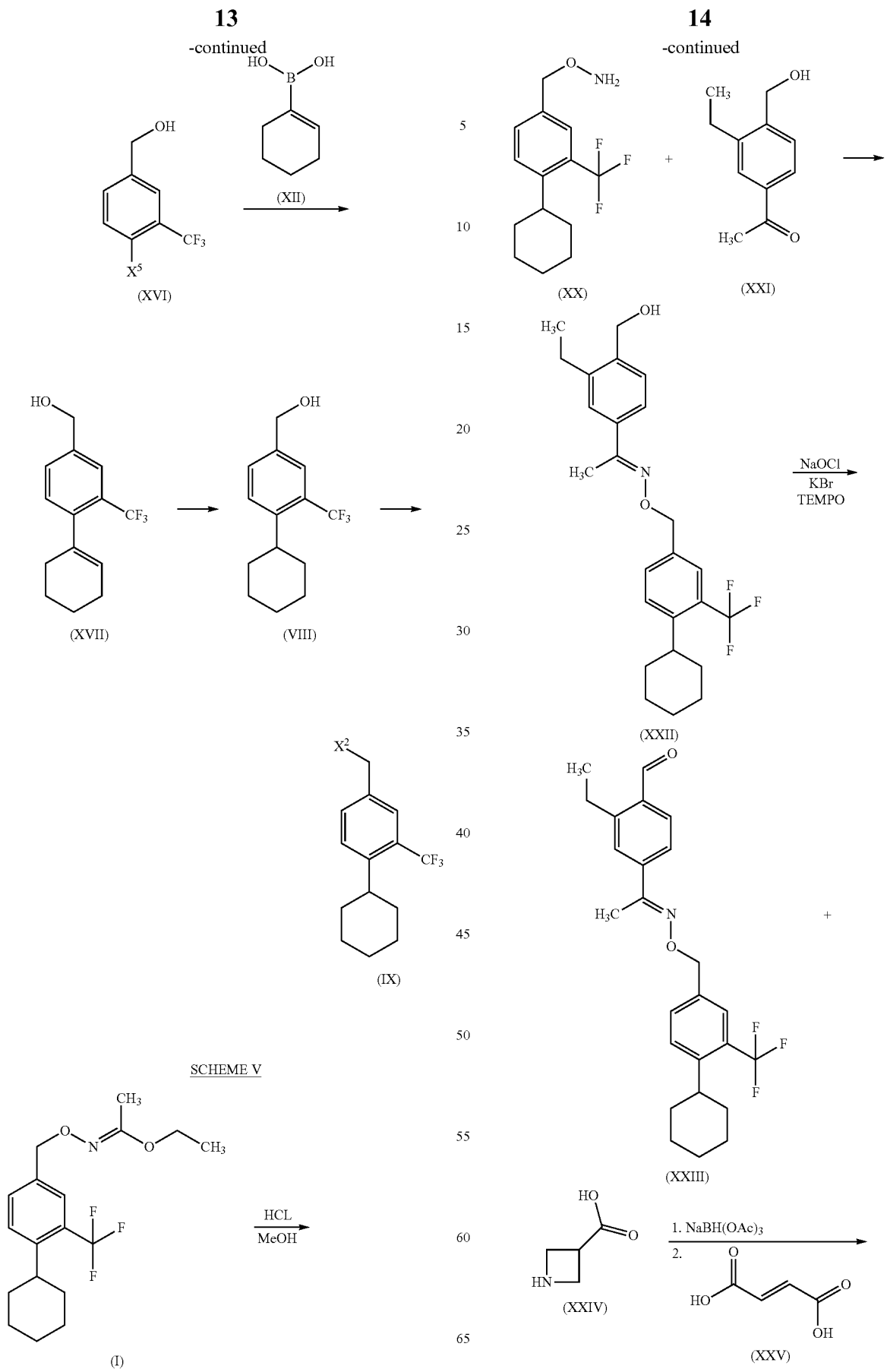

-continued

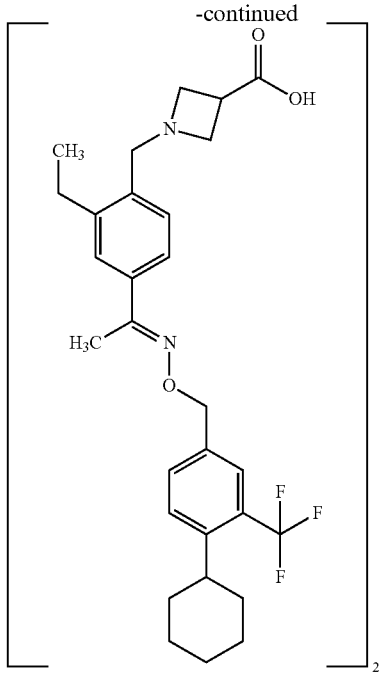
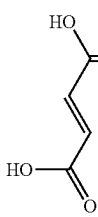

Hemifumarate salt of Compound A

Scheme 1 illustrates a method of synthesizing the compound of formula I from a compound of the formula IX, wherein the compound of formula IX is prepared by a seven step process starting with a compound of formula II. This method is advantageous in that it allows for the large scale production of the fragment of Compound A that is provided by the compound of formula I. Referring to Scheme I, a compound of the formula II, wherein X is bromo, chloro or iodo, preferably bromo, is reacted with an appropriate Grignard reagent, preferably an i-propylmagnesium chloride-lithium chloride complex, and cyclohexanone to form the compound of formula III. (When X is chloro, the Grignard compound is preferably formed by reaction with metallic magnesium, while, when X is iodo, the Grignard compound is preferably formed by an exchange with i-propylmagnesium chloride). This reaction is carried out in a solvent such as diethyl ether, tetrahydrofuran (THF), or an alkane such as hexane or heptane, or a mixture of two or more of the foregoing solvents, preferably a mixture of heptane and THF, at a temperature from about −20° C. to about 30° C., preferably from about 5° C. to about 10° C. The compound of formula III is then reacted, preferably in situ, with a strong acid such as sulfuric acid or phosphoric acid, preferably sulfuric acid, at an internal temperature (IT) from about 10° C. to about 50° C., preferably from about 20° C. to about 25° C., to form the compound of formula IV, which is then subjected to catalytic hydrogenation, using methods well known to those of skill in the art (e.g., palladium on carbon catalyst in a methanol solvent at a temperature from about 20° C. to about 50° C. and a pressure of about 2-20 bar, to produce the compound of formula V. The catalytic hydrogenation is also preferably conducted in situ.

Bromination of the compound of formula V, preferably in situ, at a temperature from about −10° C. to about 20° C., preferably from about 0° C. to about 5° C., yields the compound of formula VI wherein $X^1$ is bromo. This bromination can be accomplished by reacting the compound of formula V with 1,3-dibromo-5,5-dimethylhydantoin or N-bromosuccinimide in an acid such as sulfuric acid, trifluoroacetic acid or a mixture of sulfuric and trifluoroacetic acids, at a temperature from about −10° C. to about 5° C., preferably from about 0° C. to about 5° C. The resulting halogenated compound of formula VI can then be converted into the corresponding carboxylic acid of formula VII by reacting it, preferably in situ, with an appropriate Grignard reagent (preferably a butyl lithium butyl magnesium chloride complex or a butyl lithium i-propylmagnesiumchloride complex) and carbon dioxide. Conducting this halogenation reaction with the appropriate analogous reagents will yield the corresponding compounds of formula VI wherein X is chloro, fluoro or iodo. The carbon dioxide is preferably bubbled through the reaction mixture. Suitable temperatures for this reaction range from about −20° C. to about 20° C., preferably from about −5° C. to about 5° C. Suitable solvents include diethyl ether, THF, methyltetrahydrofuran and alkanes such as heptane or hexane, with THF being preferred. Alternatively, if this reaction is conducted with dimethylformamide being added to the reaction mixture, the aldehyde (VIIA) corresponding to the carboxylic acid of formula VII is formed. This aldehyde is a liquid at room temperature, making purification of the aldehyde by crystallization impossible. Therefore, when the aldehyde is formed and carried forward in the process, as described below, impurities from the preceding steps, including the unwanted regioisomers of compound IV, will be carried through to the formation of the compound of formula I.

Reduction of the compound of formula VII, VIIA or VIII yields the compound of formula VIII. This reduction can be accomplished using a number of reducing agents well known to those of skill in the art (e.g., borane tetrandrofurane complex, sodium borohydride/aluminum trichloride, aluminum hydride, lithium trimethoxyborohydride or lithium aluminum hydride). Lithium aluminum hydride is preferred. This reaction is generally carried out at a temperature from about −10° C. to about 60° C., preferably from about 20° C. to about 50° C. Suitable solvents include ethers (e.g., diethyl ether, dipropyl ether or THF), toluene or alkanes (e.g., heptane, hexane or cyclohexane), or a mixture one or more of the foregoing solvents. A mixture of toluene and THF is preferred.

The compound of formula VIII can be converted into the desired compound of formula IX wherein the hydroxide group is replaced with a leaving group such as bromine, chlorine, mesylate, tosylate, trilate, brosylate, phosphonate or another suitable leaving group. Leaving groups and methods of adding them to organic compounds are well known to those of skill in the art. (See Wuts, Peter G. M. and Greene, Theodore W., *Greene's Protective Groups in Organic Synthesis*, 4$^{th}$ Edition, Wiley, 2006, Print ISBN: 978-0-471-69754-1, Online ISBN: 9780470053485). Bromine is a preferred leaving group. Bromine, chlorine and iodine can be added by reacting the compound of formula VIII with hydrogen bromide, hydrogen chloride, or hydrogen iodide, respectively. This reaction is generally carried out in a solvent such as acetic acid, acetic anhydride, or sulfuric acid, preferably a mixture of acetic acid and acetic anhydride, at a temperature from about 0° C. to about 60° C., preferably from about 20° C. to about 30° C. Mesylate, triflate, tosylate and brosylate groups can be added by reacting the compound of formula VIII with, respectively, mesyl chloride, trifluoromesyl chloride, tosyl chloride and brosyl chloride in a solvent, e.g., an ether such as diethyl ether, dipropyl ether or THF, toluene or an alkane such as heptane, hexane or cyclohexane, or a mixture of one or more of the foregoing solvents, with a mixture of toluene and THF being preferred, at a temperature from about −10° C. to about 60° C., preferably from about 0° C. to about 20° C., in the presence of a base such as triethylamine, N,N-diisopropylethylamine, or pyridine. Alternatively, this reaction can be conducted in a two phase system using an aqueous base such as sodium hydroxide, sodium carbonate, potassium hydroxide or potassium carbonate, and an organic solvent such as toluene, methylene chloride or alkanes such as heptane, hexane or cyclohexane, or a mixture thereof, with toluene being preferred.

The resulting compound of formula IX can be converted into the compound of formula I by reacting it with the compound of formula X

wherein Et is ethyl, in the presence of a strong base such as sodium hydride or potassium t-butoxide, lithium diisopropylamide, or potassium, lithium or sodium hexamethyldisilazide, preferably, sodium hydride or potassium t-butoxide, in a reaction inert solvent such as dimthylformamide (DMF), N-methylpyrrolidone (NMP), THF, methyltetrahydrofurane, toluene, an alkane such as hexane or heptane, a dialkyl ether such as ethyl ether, diiosopropylether, t-butylmethyl ether or methylcyclopentylether, or a mixture of two or more of the foregoing solvents, preferably, THF, at a temperature from about −29° C. to about 40° C., preferably from about 0° C. to about 10° C. Alternatively, the above reaction can be carried in the presence of a weaker base such as potassium carbonate, sodium carbonate, and a catalytic amount of 4-dimethylaminopyridine (DMAP), at the temperatures indicated immediately above, in a solvent such as acetone, methylethylketone, or cyclohexanone, preferably acetone.

Scheme 2 provides an alternate method of synthesizing the compound of formula IX. This process, which involves only three steps, is also useful for large scale production. Referring to Scheme 2, the compound of formula XI, wherein $X^4$ is bromo, chloro or iodo, and the boronic acid of formula XII are subjected to a Suzuki Coupling reaction. This reaction is generally conducted in the presence of a palladium catalyst such as tetrakis(triphenylphoshine)palladium(0) or a mixture of a palladium (II) salt (e.g., palladium dichloride, palladium diacetate, or bistriphenylphosphinepalladium dichloride) and a phosphine (e.g., triphenylphosphine, tri-t-butylphosphine or tricyclohexylphosphine), and a base such as sodium methylate, potassium carbonate, cesium carbonate, or potassium t-butoxide, preferably sodium methylate, at a temperature from about 10° C. to about 140° C., preferably from about 90° C. to about 110° C. Suitable solvents for this reaction include dimethylformamide (DMF), dioxane, alcohols such as ethanol, methanol or i-propanol, toluene and esters such as ethylacetate and i-propylacetate. Methanol is preferred. The resulting compound of formula XIII is then subjected to catalytic hydrogenation, using methods well known to those of skill in the art (e.g., palladium on carbon catalyst in an acetic acid solvent at about 25° C. and a pressure of about 1-20 atm) to produce the compound of formula XIV.

Conversion of the compound of formula XIV to the desired compound of formula IX is accomplished by subjecting the compound of formula XIV to a halogenation reaction. The halogenation can be via a radical bromination or radical chlorination reaction, to produce a compound of the formula IX wherein $X^2$ is, respectively, chloro or bromo. Preferably, the reaction is a radical bromination, which is carried out by reacting the compound of formula XIV with N-bromosuccinimide, bromine, or 1,3-dimthyl-2,5-dibromohydantoine and a radical starter such as azoisobutyronitrile, preferably, N-bromosuccinimide, in a halogenated solvent such as dichloromethane or chlorobenzene, acetonitrile, i-ppropylacetate, or an alkane such as hexane, heptane or cyclohexane, preferably acetonitrile. The reaction temperature can range from about −20° C. to about 50° C., and is preferably about 20° C. Radical chlorination can be carried out under similar conditions, using suitable chlorinated reactants such as N-chlorosuccinimide or chlorine, preferably N-chlorosuccinimide.

Scheme 3 provides another alternate method of synthesizing compounds of the formula IX. This process, which involves only four steps, is also useful for large scale production. Referring to Scheme 3, a compound of the formula XV, wherein $X^5$ is chloro, bromo or iodo, is reacted with a strong reducing agent (e.g., borane tetrandrofurane complex, sodium borohydride/aluminum trichloride, aluminum hydride, lithium trimethoxyborohydride or lithium aluminum hydride), preferably lithium aluminum hydride, to form the corresponding compound of formula XVI wherein $X^5$ is, respectively, chloro, bromo or iodo. This reaction is generally carried out at a temperature from about −10° C. to about 60° C., preferably from about 20° C. to about 50° C. Suitable solvents include ethers such as diethyl ether, dipropyl ether or THF, toluene and alkanes such as heptane, hexane or cyclohexane, or a mixture thereof, with a mixture of toluene and THF being preferred. A Suzuki Coupling of the resulting compound of formula XVI with the boronic acid of formula XII, using conditions well known to those of skill in the art and referred to above in the discussion of Scheme 2, yields the compound of formula XVII. The compound of formula XVII can be converted into the compound of formula VIII via catalytic hydrogenation, using conditions well known to those of skill in the art (e.g., palladium on carbon catalyst in an acetic acid solvent at about 25° C. and a pressure of about 1-20 atm). The conversion of the compound of formula VIII to the desired compound of formula IX can be accomplished as described above in the discussion of reaction Scheme I.

Scheme 4 illustrates another alternate method of synthesizing the compound of formula IX. This process also involves only four steps and is also useful for large scale production. Referring to Scheme 4, a compound of the formula XV, wherein $X^5$ is chloro, bromo or iodo, and the boronic acid of formula XII are subjected to a Suzuki Coupling reaction, using conditions well known to those of skill in the art and referred to above in the discussion of Scheme 2, to form the compound of formula XIX. The compound of formula XIX is then subjected to catalytic hydrogenation, using conditions well known to those of skill in the art (e.g., palladium on carbon catalyst in an acetic acid solvent at about 25° C. and a pressure of about 1-20 atm), to produce the compound of formula VII, which can then be converted into the desired compound of formula IX via the compound of formula VIII, as described above in the discussion of the reaction chain VII→VIII→IX in Scheme 1.

A process by which Compound A can by synthesized from the compound of formula I is depicted in Scheme 5. Referring to Scheme 5, a solution of the compound of formula I in a solvent such as methanol, propanol or i-propanol and at a temperature from about −20° C. to about 40° C., preferably at about 20° C., is treated with hydrochloric acid or sulfuric acid, preferably hydrochloric acid, to generate the oxime of formula XX, which is then reacted with compound of formula XXI to form the compound of formula XXII. The reaction of the compounds of formulas XX and XXI is generally conducted in an alcoholic solvent such as methanol, ethanol, isopropanol, or butanol. Methanol is preferred. Suitable reaction temperatures can range from about 0° C. to about 60° C., with the preferred temperature being from about 20° C. to about 40° C. The resulting compound of formula XXII is then dissolved in a solvent such as toluene, acetonitrile, methylene chloride, or alkanes such as hexane, heptanes or cyclohexane, or mixture of two or more of the foregoing solvents, preferably a mixture of toluene and ethyl acetate, and oxidized to form the compound of formula XXIII by the addition of an aqueous solution of potassium bromide and potassium bicarbonate and a catalytic amount of TEMPO (2,2,6,6-tetramethylpiperidine 1-oxyl) or poly [[6-[(1,1,3,3-tetramnethylbutyl)amino]-1,3,5-triazine-2,4-diyl]][(2,2,6,6-tetramethyl-1-oxy-4-piperidinyl)imino]-1,6-hexanediyl[(2,2,6,6-tetramethyl-1-oxy-4-piperidinyl) imino]]) (PIPO), followed by an aqueous solution of sodium hypochlorite. This reaction is generally conducted at a temperature from about −20° C. to about 50° C., with the preferred temperature being from about 10° C. to about 20° C. Alternatively, the compound of formula XXII in a solution of heptanes can be oxidized to form the compound of formula XXIII by the addition of manganese dioxide.

Reductive amination of the compound of formula XXIII, using methods well known to those of skill in the art, preferably with azetidine-3-carboxylic acid and sodium triacetoxyborohydride in methanol, followed by salt formation using methods well known to those of skill in the art, e.g., with fumaric acid in ethanol, followed by recrystallization from acetone/water, yeilds the hemifumarate salt of Compound A.

EXPERIMENTAL EXAMPLES

The following experimental examples illustrate the processes of the present invention and are not intended to limit the scope of such invention.

Example 1

Synthesis of
1-Cyclohex-1-enyl-2-trifluoromethyl-benzene 200 ml i-Propylmagnesiumchlorid-LiCl complex 1.3M in THF were placed in a dry reactor at room temperature (RT) under Argon and cooled to IT=5-10° C. Then 27.5 ml 2-Brombenzotrifluorid was added within 1 hour (h) keeping IT at 5-10° C. The resulting mixture was stirred for 1 h at IT=5-10° C. Then a solvent change from THF to heptanes was performed by distilling off THF while adding 120 ml heptanes, keeping the volume of the reaction constant. To the obtained suspension, 23.1 ml Cyclohexanone was added within 1 h keeping IT at 15-25° C. The resulting emulsion was stirred at IT=15-25° C. for 1-2 h. After completion the reaction was quenched by the addition of 147 g $H_2SO_4$ 10% at IT=20-30° C. The phases were separated, the aqueous phase extracted with 14.2 ml heptanes and the combined organic phases were washed with 13.5 ml water. The organic phase was concentrated to a volume of 120 ml and 42.1 g $H_2SO_4$ 90% were added within 1 h keeping IT at 20-25° C. The resulting mixture is stirred at high speed until the conversion from compound III to compound IV is complete. Then the phases were separated, the sulfuric acid phase extracted with 10 ml heptanes. To the combined organic phases 1.46 g Sodium acetate, 1 g Silicagel, 1 g charcoal and 1 ml Water were added. The mixture was filtrated over a nutsch filter covered with cellflock and the filtrate was evaporated to dryness giving 35.4 g of 1-Cyclohex-1-enyl-2-trifluoromethyl-benzene which was used without further purification for the synthesis of 1-Cyclohexyl-2-trifluoromethyl-benzene

$^1$H-NMR (400 MHz, DMSO-d6): δ 1.5-1.7(4H,m), 2.1-2.2(4H,m), 5.51(1H,m), 7.29(1H,d), 7.44(1H,t), 7.59(1H,t), 7.68(1H,d) MS:(ES−): 226 (M+)

Example 2

Synthesis of
1-Cyclohexyl-2-trifluoromethyl-benzene

In a hydrogenation reactor 8.45 g 1-Cyclohexyl-2-trifluoromethyl-benzene were dissolved in 42 ml methanol. 1.33 g Palladium 10% on Charcoal water wet was added and the reaction mixture hydrogenated with hydrogen gas at IT=40° C. and 1-5 Bar until the uptake of hydrogen stopped. After filtration over Hyflo, the filtrate was evaporated to dryness and degassed. Heptanes (40 ml) were added and the mixture was evaporated to dryness and degassed again. This gave 7.64 g 1-cyclohexyl-2-trifluoromethyl-benzene as a slightly turbid yellow oil which was used without further purification for the synthesis of 4-bromo-1-cyclohexyl-2-trifluoromethyl-benzene.

$^1$H-NMR (400 MHz, CDCl3): δ 1.35-1.9(10H,m), 2.85-3(1H,m) 7.2-7.3(1H,m) 7.4-7.5(2h,m), 7.55-7.65(1H,m).

Example 3

Synthesis of
4-Bromo-1-cyclohexyl-2-trifluoromethyl-benzene

1-Cyclohexyl-2-trifluoromethyl-benzene (38.8 g) was dissolved in 126.4 trifluoroacetic acid at 20-25° C. Then the solution was cooled to IT=0-5° C. and 17.19 g $H_2SO_4$ (ca 96%) were added. To the resulting orange suspension 26.73 g 1,3-dibromo-5,5-dimethylhydantoin were added in 6 portions within 1-2 h at IT=0-5° C. Thirty minutes after the last addition, an in process control was performed and more 1,3-dibromo-5,5-dimethylhydantoin was added on an as needed basis. When the bromination was complete, 67.5 g heptanes were added and the mixture was stirred for 5-10 minutes (min.) followed by phase separation at IT=20-25° C. The lower inorganic phase was extracted a second time with 33.8 ml heptanes. The combined organic phases were extracted with 57.85 g 10% Na-hydrogensulfite in water followed by 55.4 g 2N NaOH and three times 41 g water. Charcoal (0.61 g) was added to the organic phase and the mixture was stirred 1 h at RT. After filtration, the filtrate was dried by isotropic distillation and evaporated to dryness. This gave 49.6 g of 4-bromo-1-cyclohexyl-2-trifluoromethyl-benzene as a yellow oil, which was used without further purification for the synthesis of 4-cyclohexyl-3-trifluoromethyl-benzoic acid.

¹H-NMR (400 MHz, DMSO-d6): δ 1.2-1.9(10H,m), 2.76 (1H, T), 7.55-7.61(1H,d), 7.76.7.85(2H,m)

Example 4

Synthesis of
4-Cyclohexyl-3-trifluoromethyl-benzoic acid

In a dry vessel, 61.4 g 4-bromo-1-cyclohexyl-2-trifluoromethyl-benzene were dissolved in 230 ml tetrahydrofurane under nitrogen. i-Propylmagnesiumchloride (2M, 36.1 ml) in tetrahydrfuran (THF) were added within 15-30 min. Then the reaction mixture was cooled to IT=−5-+5° C. and 88 ml 1.6M butyllithium in hexane were added from an addition funnel keeping IT=−5-+5° C. within 1-2 h. To this solution 17.6 g $CO_2$ were added within 1-2 h at IT=−5 to +5° C. When the reaction was complete, the reaction was quenched by the drop wise addition of 160 ml 2M $H_2SO_4$, keeping IT at −5-20° C. The phases were separated and the organic phase was washed with 2 times 100 ml water and concentrated to a volume of approx. (approximately) 160 ml. A solvent change to toluene was performed. The volume of the toluene solution was then adjusted to about 180 ml and heated until a clear solution was obtained. Upon cooling to 0° C., 4-cyclohexyl-3-trifluoromethyl-benzoic acid crystallized out and was isolated by filtration followed by drying in a vacuum oven at 60° C. over night. This gave 4-cyclohexyl-3-trifluoromethyl-benzoic acid as a white crystalline solid with a purity of >99%(F) by HPLC and a mp. of 206.7-208° C. ¹H-NMR (400 MHz, DMSO-d6): δ 1.2-1.8 (10H, m), 2.85(1H, m), 7.7-8.1(3H, m), 13.31(1H, s) MS: ($ES^-$): 271(M−1).

Example 5

Synthesis of
4-Cyclohexyl-3-trifluoromethyl-phenyl)-methanol

4-Cyclohexyl-3-trifluoromethyl-benzoic acid (119.8 g) was suspended in 300 ml toluene at 20-25° C. To this suspension 120 ml 3.5M $LiAlH_4$ in toluene/THF was added, keeping IT at 20-50° C. When the reaction was completed, the reaction mixture was carefully added to a mixture of 420 ml water and 117 ml 96% $H_2SO_4$ keeping the internal temperature at 15-25° C. Then the phases were separated and the aqueous phase was washed with 40 ml toluene. The combined toluene phases were concentrated to a volume of 240 ml. This solution of 4-cyclohexyl-3-trifluoromethylphenyl)-methanol was used, without purification, for the synthesis of 4-bromomethyl-1-cyclohexyl-2-trifluoromethyl-benzene.
¹H-NMR (400 MHz, DMSO-d6): δ 1.2-1.8(10H,m), 2.79 (1H,t), 4.52(2H,d), 5.30(1H,t), 7.5-7.6(3H,m) MS: 241 ($MH-H_2O$), 276 ($M+NH4^+$)

Example 6

Synthesis of 4-Bromomethyl-1-cyclohexyl-2-trifluoro-methyl-benzene

To the solution of 4-yclohexyl-3-trifluoromethyl-phenyl)-methanol from Example 6, 340 ml HBr 5.7M in acetic acid were added at IT=20-30° C. within 15-30 min. To the resulting emulsion 34 ml acetic anhydride were added, keeping IT at 20-25° C. The reaction mixture was stirred at IT=20-25° C. until the reaction was complete. The mixture was then quenched by the addition of 200 ml water. Heptanes (340 ml) were added and the phases were separated. The organic phase was washed with 240 ml $NaHCO_3$ solution (ca 1M) followed by 120 ml water. Azeotropic drying and evaporation to dryness gave 4-bromomethyl-1-cyclohexyl-2-trifluoro-methyl-benzene as a clear yellow oil, which was used, without purification, for the synthesis of N-(4-cyclohexyl-3-trifluoromethylbenzy-loxy)-acetimidic acid ethyl ester
¹H-NMR (400 MHz, CDCl3): δ 1.2-1.8(10H, m), 2.93 (1H,t), 4.49(2H,s), 7.44(1H,d), 7.53(1H,d), 7.62(1H,d) MS:320,322 $M^+$, 241 $M-Br^+$

Example 7

Synthesis of N-(4-Cyclohexyl-3-trifluoromethylbenzyloxy)-acetimidic acid ethyl ester 4-Bromomethyl-1-cyclohexyl-2-trifluoro-methyl-benzene (68.25 g) and 50 g N-hydroxy-acetimidic acid ethyl ester as a 50% solution in $CH_2Cl_2$ were dissolved in 350 ml acetone. To this solution 1.17 g 4-dimethylaminopyridine and 139 g potassium carbonate were added. This suspension was stirred at IT=50-52° C. until the reaction was complete. Then the mixture was cooled to 20-25° C., filtrated and a solvent was changed to t-butylmethylether. The solution in t-butylmethylether was adjusted to a volume of 400 ml and extracted with 150 ml water 2×, followed by 100 ml brine. Evaporation to dryness gave 66.7 g of N-(4-cyclohexyl-3-trifluoromethylbenzy-loxy)-acetimidic acid ethyl ester as a yellow oil, which was used, without purification, for the synthesis of 1-(3-Ethyl-4-hydroxymethyl-phenyl)-ethanone O-(4-cyclohexyl-3-trifluoromethyl-benzyl)-oxime
¹H-NMR (400 MHz, DMSO-d6): δ 1.26 (3H, t), 1.35-1.9 (10H,m), 1.96(3H,s), 2.93(1H,m), 3.99-4.03(2H,q), 4.92 (2H,s), 7.4-7.6(3H,m), MS ($ES^+$): 344 ($MH^+$)

Example 8

Synthesis of N-(4-Cyclohexyl-3-trifluoromethylbenzyloxy)-acetimidic acid ethyl ester In a dry vessel, 39.7 g N-Hydroxy-acetimidic acid ethyl ester as a 50% solution in tetrahydrofurane were added to 200 ml of tetrahydrofurane. To this solution 123.4 g of a 20% solution of potassium t-butylate in THF was added within 1 h, keeping IT at 0-5° C. After stirring this solution for 2 h (IT at 0-5° C.), a solution of 70 g 4-bromomethyl-1-cyclohexyl-2-trifluoro-methyl-benzene in 70 ml tetrahydrofurane was added within 2 h, keeping IT at 0-5° C. After completion of the reaction, the mixture was quenched by the addition of 200 ml ethylacetate and 200 ml water. The phases are separated and the organic phase was washed twice with 200 ml NaCl solution (2% in water). Evaporation, addition of 200 ml Ethylacetate and evaporation to dryness gave 66.1 g N-(4-cyclohexyl-3-trifluoromethylbenzyloxy)-acetimidic acid ethyl ester as a yellow oil, which was used without further purification for the synthesis of 1-(3-Ethyl-4-hydroxymethyl-phenyl)-ethanone O-(4-cyclohexyl-3-trifluoromethyl-benzyl)-oxime.
¹H-NMR (400 MHz, DMSO-d6): δ 1.26 (3H,t), 1.35-1.9 (10H,m), 1.96(3H,s), 2.93(1H,m), 3.99-4.03(2H,q), 4.92 (2H,s), 7.4-7.6(3H,m), MS($ES^+$): 344($MH^+$)

Example 9

Synthesis of 1-(3-Ethyl-4-hydroxymethyl-phenyl)-ethanone O-(4-cyclohexyl-3-trifluoro-methyl-benzyl)-oxime N-(4-Cyclohexyl-3-trifluoromethylbenzy-loxy)-acetimidic acid ethyl ester (42.9 g) was dissolved in 306 ml methanol. To this 20.1 ml 36% HCl were added, keeping IT=20-25° C. The mixture was stirred at IT=20-25° C. for 30-40 min. Then the pH was adjusted to 4.5 by the addition of ca 30 ml triethylamine. Then 21.4 g 1-(3-ethyl-4-hydroxymethyl-phenyl)-ethanone dissolved in 87 ml methanol were added at IT=20-25° C. within 5-10 min. The reaction mass was stirred at IT=20-25° C. for 20-24 h. During this time, the pH dropped to 0-1. After the reaction went to completion, the methanol was distilled off at AT=30-50° C./200-120 mbar within 1-5 h. To the distillation residue 290 ml i-propylacetate followed by 130 ml water were added. The phases were separated and the organic phase was washed with 200 ml 1 M NaHCO$_3$ solution in water, followed by a mixture of 200 ml demineralised water and 20 ml brine. The organic phase was concentrated at the rotary evaporator (AT=30-40° C./120-10 mbar) to a volume of 100 ml. The distillation residue was dissolved in 250 ml toluene and again evaporated to dryness. This gave 57 g 1-(3-ethyl-4-hydroxymethyl-phenyl)-ethanone O-(4-cyclohexyl-3-trifluoro-methyl-benzyl)-oxime as a slightly yellow oil, which was used without further purification for the synthesis of 4-{1-[(E)-4-Cyclohexyl-3-trifluoromethyl-benzyloxyimino]-ethyl}-2-ethyl-benzaldehyde.

Example 10

Synthesis of 4-{1-[(E)-4-Cyclohexyl-3-trifluoromethyl-benzyloxy-imino]-ethyl}-2-ethyl-benzaldehyde 1-(3-Ethyl-4-hydroxymethyl-phenyl)ethanone O-(4-cyclohexyl-3-trifluoro-methyl-benzyl)-oxime (45 g) was dissolved in 134 ml heptanes. To this solution 59.7 g manganese dioxide were added in one portion and washed down with 43 ml heptanes. The reaction mixture was stirred at IT=50-55° C. until the reaction went to completion. Then it was filtrated over a Nutsche filter with CEFOK. The filtrate was evaporated to dryness and dissolved in 60 ml i-propanol containing 2 ml water by heating to reflux. Upon cooling to 0° C., 4-{1-[(E)-4-cyclohexyl-3-trifluoromethyl-benzyloxy-imino]-ethyl}-2-ethyl-benzaldehyde crystallized out and was isolated by filtration. Drying over night in a vacuum oven at 60° C. gave 22 g 4-{1-[(E)-4-cyclohexyl-3-trifluoromethyl-benzyloxy-imino]-ethyl}-2-ethyl-benzaldehyde as a white crystalline solid, which was further purified by crystallization from i-propanol containing 3% water.

$^1$H-NMR (400 MHz, DMSO-d6): δ 1.20(3H, t), 1.34(6H, m), 1.4-1.8 (10H,m), 2.28 (3H,s), 2.82(1H,m)3.05(2H,q), 5.30(2H,s), 7.6-7.88 (6H,m), 10.27(1H,s) MS:(ES$^+$):432 (M+1) Mp.:80.5-81.5° C.

Example 11

Synthesis of 4-{1-[(E)-4-Cyclohexyl-3-trifluoromethyl-benzyloxy-imino]-ethyl}-2-ethyl-benzaldehyde 1-(3-Ethyl-4-hydroxymethyl-phenyl)ethanone O-(4-cyclohexyl-3-trifluoro-methyl-benzyl)-oxime (57 g) was dissolved in 176 ml toluene and 176 ml ethylacetate. To this solution 183 mg TEMPO, followed by 31.18 g ca 25% KBr solution and 135.5 g ca 14% KHCO$_3$ solution were added within 10-30 min. The mixture was cooled to IT=10-20° C. and 94 g NaOCl solution 10.9% were added with intensive stirring at IT=10-20° within 30-60 min. The reaction mixture was stirred for 30 min and, when an in process control showed complete conversion, quenched by the addition of 87 g 10% Na-thiosulfate solution at IT=20-25° C. The phases were separated and then the organic phase was washed with 2×100 ml water. Then the organic phase was concentrated to a volume of 55 ml and 90 ml i-Propanol containing 3% H$_2$O (water) were added and the mixture was again distilled to a volume of 55 ml. 90 ml i-Propanol containing 3% H$_2$O were added and the mixture was heated to IT=60-65° C. to obtain a clear solution. Upon cooling to 0° C., crude 4-{1-[(E)-4-cyclohexyl-3-trifluoromethyl-benzyloxy-imino]-ethyl}-2-ethyl-benzaldehyde crystallized out and was isolated by filtration. The wet cake was again recrystallized from 50 ml i-propanol containing 3% water. After drying overnight in a vacuum oven at 40° C., 35.5 g 4-{1-[(E)-4-cyclohexyl-3-trifluoromethyl-benzyloxy-imino]-ethyl}-2-ethyl-benzaldehyde was obtained as a slightly yellow powder.

$^1$H-NMR (400 MHz, DMSO-d6): δ 1.20(3H,t), 1.34(6H, m), 1.4-1.8(10H,m), 2.28 (3H, s), 2.82(1H,m)3.05(2H,q), 5.30(2H,s), 7.6-7.88(6H,m), 10.27(1H,s) MS:(ES$^+$):432 (M+1)

Example 12

Synthesis of 1-(4-{1-[(E)-4-Cyclohexyl-3-trifluoromethyl-benzyloxyimino]-ethyl}-2-ethyl-benzyl)-azetidine-3-carboxylic acid hemifumarate 4-{1-[(E)-4-Cyclohexyl-3-trifluoromethyl-benzyloxy-imino]-ethyl}-2-ethyl-benzaldehyde (15 g) and 4.93 g azetidine-3-carboxylic acid were suspended in 260 ml methanol and stirred for 30 min at 20-25° C. Then 13.97 g sodium triacetoxyborohydride were added within 1-2 h in 8 portions of 1.75 g at IT=20-25° C. The reaction was stirred until an in process control showed complete conversion to 1-(4-{1-[(E)-4-cyclohexyl-3-trifluoromethyl-benzyloxyimino]-ethyl}-2-ethyl-benzyl)-azetidine-3-carboxylic acid. Then methanol was distilled off to a volume of 50 ml. 180 ml ethyl acetate and 90 ml water were added and the pH was adjusted to 6 by the addition of about 40 ml 2M NaOH. The phases were separated and the organic phase was washed with 35 ml water. The organic phase was distilled to a volume of 100 ml; 100 ml 100% ethanol were added and the organic phase was again distilled to a volume of 100 ml. A second portion of 100 ml 100% ethanol was added and the organic phase was again distilled to 100 ml. Then 100 ml 100% ethanol were added, together with 1.5 g charcoal and 1.5 g Hyflo. The resulting suspension was stirred for 30 min at 20-25° C., filtrated and concentrated to a volume of 140 ml. Then 10 ml of a preheated (50° C.) 3% solution of a fumaric acid in 100% ethanol was added at IT=50° C. The solution was seeded with 1-(4-{1-[(E)-4-cyclohexyl-3-trifluoromethyl-benzyloxyimino]-ethyl}-2-ethyl-benzyl)-azetidine-3-carboxylic acid hemifumarate, and after the crystallization has started, 90.1 g of a 3% solution of a fumaric acid in 100% ethanol was added within 30 min-1 h at IT=50° C. The suspension was slowly cooled to 20° C., filtrated and dried in a vacuum oven at 40° C. overnight. This gave 15.34 g 1-(4-{1-[(E)-4-cyclohexyl-3-trifluoromethyl-benzyloxy-imino]-ethyl}-2-ethyl-benzyl)-azetidine-3-carboxylic acid hemifumarate.

$^1$H-NMR (400 MHz, DMSO-d6): δ 1.14(3H,t), 1.25-1.85 (10H,m), 2.2(3H,s), 2.6-2.7(2H,q), 2.75-2.85(1H,t), 3.17-3.28(3H,m), 3.38-3.46(2H,m), 3.6 (2H,s), 5.21(2H,s), 6.61 (1H,s), 7.22-7.7 (6H,m)

Example 13

Synthesis of 4-Cyclohex-1-enyl-3-trifluoromethyl-benzoic acid

In pressure reactor 20 g 4-bromo-3-(trifluoromethyl)benzoic acid, 9.37 g cyclohexenylboronic acid, 0.52 g bis (triphenylphosphine)palladium (II) chloride and 15.41 g potassium carbonate in 150 ml methanol were carefully degassed and stirred under nitrogen at IT 95° C. until the reaction went to completion (3-4 h). Ethylacetate (250 ml) and 200 ml 0.1N HCl were added to the reaction mixture at IT=20-25° C. The phases were separated and the organic phase was washed with 2×159 ml 10% NaCl in water. Then 5 g charcoal were added to the organic phase, and the mixture is stirred for 30 min and filtrated. Evaporation to dryness gave 20.02 g of an orange solid which contained ca 94% 4-cyclohex-1-enyl-3-trifluoromethyl-benzoic acid according to HPLC. This is used without further purification for the synthesis of 4-cyclohexyl-3-trifluoromethyl-benzoic acid $^1$H-NMR (400 MHz, DMSO-d6): δ 1.6-1.8(4H,m), 2.1-2.3(4H,m), 5.58(1H,t), 7.48(1H,d), 8.12-8.17(2H,m) MS: 269.0799(M-H)$^-$ Example 14

Synthesis of 4-Cyclohexyl-3-trifluoromethyl-benzoic acid

In a hydrogenation reactor, 18.0 g 4-cyclohex-1-enyl-3-trifluoromethyl-benzoic acid were dissolved in 150 ml methanol and 10% 7.1 g palladium on charcoal were added. After 15 h hydrogenation at 4.5 bar/50° C. the starting material was consumed. Filtration and evaporation to dryness gave 16 g of a solid, which was recrystallized from 110 ml toluene to give 12.9 g 4-cyclohexyl-3-trifluoromethyl-benzoic acid, which, according to HPLC and $^1$H-NMR, was identical to the 4-cyclohexyl-3-trifluoromethyl-benzoic acid of Example 4.

Example 15

Synthesis of 1-Cyclohex-1-enyl-4-methyl-2-trifluoromethyl-benzene

In a pressure tube, 2.575 g 1-bromo-4-methyl-2-(trifluoromethyl)benzene, 1.839 g cyclohexenylboronic acid, 0.075 g Bis[Triphenylphosphin]Pdalladiumdichloride and 7.317 ml sodium methanolate were dissolved in 13 ml methanol. This mixture was stirred at AT=100° C. until the reaction was completed. The reaction mixture was cooled to 20-25° C. and evaporated to dryness. The residue was dissolved in a 2:1 mixture of heptanes and ethyl acetate. The solution was washed with aqueous NH$_4$Cl solution followed by aqueous K$_2$CO$_3$ solution, dried over Na$_2$SO$_4$, filtrated over a small pad of silica gel and evaporated to dryness. This gave 2.25 g of 1-cyclohex-1-enyl-4-methyl-2-trifluoromethyl-benzene as colorless oil, which was used without further purification for the synthesis of 1-cyclohexyl-4-methyl-2-trifluoromethyl-benzene.

$^1$H-NMR (400 MHz, CDC$_3$): δ 1.5-2.1(8H,m), 2.28(3H, s), 5.45(1H,s), 6.9-7.3(3H,m)

Example 16

Synthesis of 1-Cyclohexyl-4-methyl-2-trifluoromethyl-benzene

In a hydrogenation reactor, 2.25 g 1-cyclohex-1-enyl-4-methyl-2-trifluoromethyl-benzene was dissolved in 15 ml methanol. Five percent Pd/C (0.399 g, water wet), was added and the mixture was hydrogenated at IT=60° C./5 bar for 16 h. After the hydrogenation went to completion, the reaction mixture was cooled to 20-25° C., filtrated and evaporated to dryness. The residue was dissolved in heptanes, washed with water, dried over Na$_2$SO$_4$ and filtrated over a small pad of Silica gel. Evaporation to dryness gave 2.27 g 1-cyclohexyl-4-methyl-2-trifluoromethyl-benzene as a colorless oil, which was used without further purification for the synthesis of 4-bromomethyl-1-cyclohexyl-2-trifluoromethyl-benzene.

$^1$H-NMR (400 MHz, CDC$_3$): δ 1.4-1.95(10H,m), 2.38 (3H,s), 2.9(1H,m), 7.2-7.5 (3H, m)

Example 17

Synthesis of 4-Bromomethyl-1-cyclohexyl-2-trifluoromethyl-benzene

In a pressure tube, 100 mg 1-cyclohexyl-4-methyl-2-trifluoromethyl-benzene was dissolved in 1.5 ml heptanes and 75 μl acetonitrile, 0.105 g N-bromosuccinimide and 3.2 mg 2,2'-azobis(2-methylpropionitrile) (AIBN) were added. This mixture was stirred over night at IT=80° C. After cooling to RT, water was added to the reaction mixture and the phases were separated. The aqueous phase was washed with cyclohexane, the combined organic phases were washed with water followed by brine and dried over Na$_2$SO$_4$. Evaporation to dryness gave a yellow oil, the main component of which, according to HPLC and $^1$H-NMR, was identical to the 4-bromomethyl-1-cyclohexyl-2-trifluoromethyl-benzene from Example 6.

The invention claimed is:
1. A process for preparing a compound of the following formula:

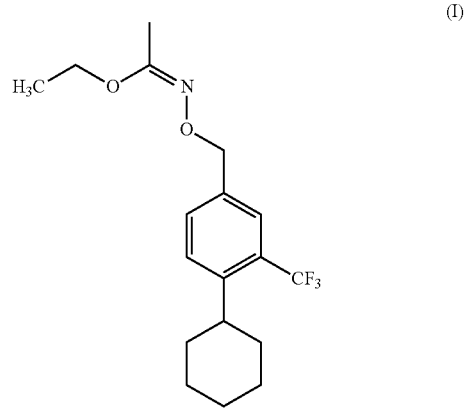 [SMILES: CCO/C(C)=N\OCc1ccc(C2CCCCC2)c(C(F)(F)F)c1]

(I)

comprising reacting a compound of the formula

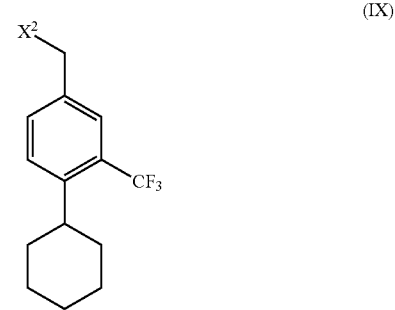

(IX)

wherein X$^2$ is bromo, chloro, iodo, mesylate, tosylate, triflate or another suitable leaving group, with the compound of formula

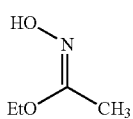

(X)

in the presence of a strong base, wherein the starting material of formula IX is synthesized comprising the steps of:

(a) reacting a compound of the formula

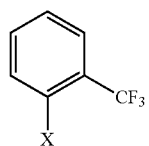

(II)

wherein X is chloro, bromo, or iodo, with a Grignard reagent to form the compound of the formula

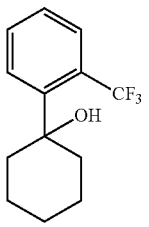

(III)

(b) reacting the compound of formula III with strong acid to form the compound of formula

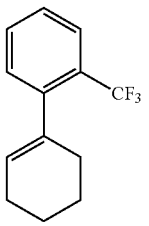

(IV)

(c) subjecting the compound of formula IV to catalytic hydration to form the compound of formula

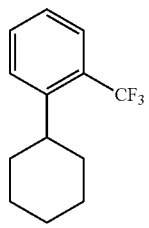

(V)

(d) converting the compound of formula V into a compound of the formula

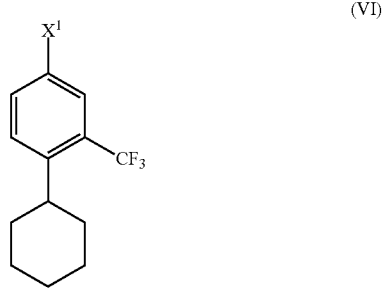

(VI)

wherein $X^1$ is bromo, chloro or iodo, by reacting the compound of formula V with 1,3-dibromyl-5,5-diethylhydantoin when $X^1$ in formula VI is bromo, or by reacting the compound of formula V with the appropriate analogous compound when $X^1$ is chloro, fluoro or iodo, in the presence of an acid;

(e) reacting the compound of formula VI with a Grignard reagent and carbon dioxide to form the compound of formula

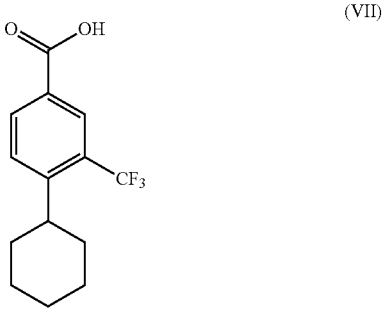 [SMILES: O=C(O)c1ccc(C2CCCCC2)c(C(F)(F)F)c1]

(VII)

or, alternatively, when carrying out the above reaction of step "e", adding dimethylformamide to the Grignard reagent to form the corresponding aldehyde of formula

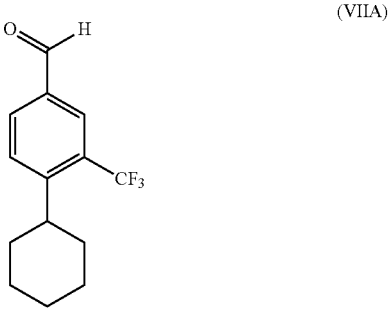 [SMILES: O=Cc1ccc(C2CCCCC2)c(C(F)(F)F)c1]

(VIIA)

(f) reducing the compound of formula VII or VIIA to form the compound of formula

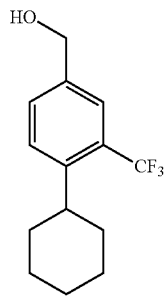

(VIII)

(g) reacting the compound of formula VIII with the appropriate compound of the formula $HX^2$, wherein $X^2$ is defined as it is for formula IX, to form the desired compound of formula IX.

2. A process according to claim 1, wherein, in step "a", X is chloro and the Grignard reagent is isopropylmagnesium chloride lithium chloride complex.

3. A process according to claim 1, wherein, in step "b", the acid is sulfuric acid.

4. A process according to claim 1, wherein, in step "d", $X^1$ is bromo.

5. A process according to claim 1, wherein, in step "d", the acid is sulfuric acid, trifluoroacetic acid or a mixture of trifluoroacetic acid and sulfuric acid.

6. A process according to claim 1, wherein, in step "e", the Grignard reagent is a butyl lithium butylmagnesiumchloride complex or a butyl lithium i-propylmagnesiumchloride complex.

7. A process according to claim 1, wherein, wherein, in step "e", an aldehyde of formula VIIA is formed.

8. A process according to claim 1, wherein, in step "f", the reducing agent is lithium aluminum hydride.

9. A process for preparing a compound of the following formula:

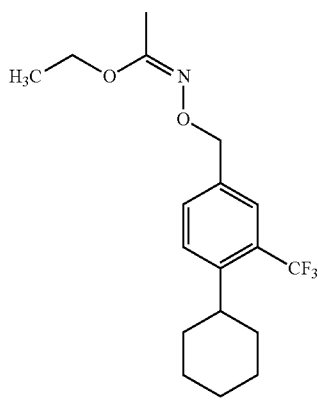

(I)

comprising reacting a compound of the formula

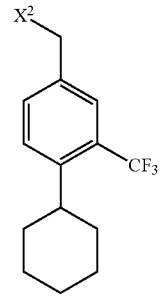

(IX)

wherein $X^2$ is bromo, chloro, iodo, mesylate, tosylate, triflate or another suitable leaving group, with the compound of formula

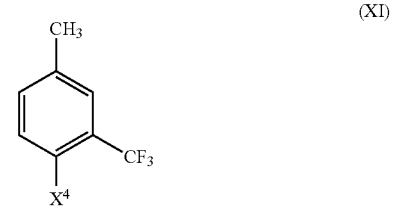

(X)

in the presence of a strong base, wherein the starting material of formula IX is synthesized comprising the steps of:

(a) reacting a compound of the formula (XI)

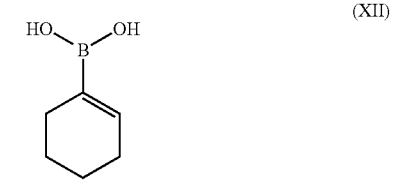

with the compound of formula (XII)

to form the compound of formula

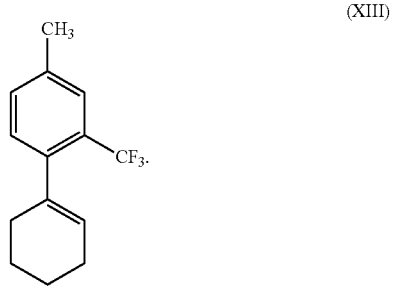 [SMILES: Cc1ccc(C2=CCCCC2)c(C(F)(F)F)c1]

(XIII)

(b) subjecting the compound of formula XIII to catalytic hydrogenation, to form the compound of formula

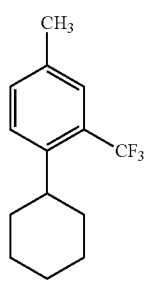

(XIV)

and (c) subjecting the compound of formula XIV to radical bromination with N-bromosuccinamide, or to standard bromination with hydrobromic acid, to form the compound of formula IX wherein $X^2$ is bromo, or, alternatively, reacting the compound of formula XIV with the appropriate compound of formula $HX^2$, wherein $X^2$ is defined as it is for formula IX, to form the desired compound of formula IX.

10. A process according to claim 9, wherein, in step "c", the compound of formula XIV is reacted with N-bromosuccinimide, bromine or 1,3-dimethyl-2,5-dibromohydantoine and a radical starter.

11. A process according to claim 10 wherein the compound of formula XIV is reacted with N-bromosuccinimide and a radical starter which is azoisobutyronitrile.

12. A process according to claim 9, wherein step "a" is conducted in the presence of a base, a phosphine and a palladium catalyst.

13. A process according to claim 12, wherein the palladium catalyst is palladium acetate and the base is sodium methylate and the phosphine is triphenylphosphine.

14. A process according to claim 9, wherein the reaction of step "a" is conducted in methanol.

* * * * *